(12) United States Patent
Adachi et al.

(10) Patent No.: US 7,728,487 B2
(45) Date of Patent: Jun. 1, 2010

(54) ULTRASOUND TRANSDUCER MANUFACTURED BY USING MICROMACHINING PROCESS, ITS DEVICE, ENDOSCOPIC ULTRASOUND DIAGNOSIS SYSTEM THEREOF, AND METHOD FOR CONTROLLING THE SAME

(75) Inventors: Hideo Adachi, Iruma (JP); Katsuhiro Wakabayashi, Tokyo (JP); Akiko Mizunuma, Tokyo (JP); Yukihiko Sawada, Yoshikawa (JP); Takuya Imahashi, Kawasaki (JP); Takanao Fujimura, Sagamihara (JP); Ki Doh, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/203,854

(22) Filed: Sep. 3, 2008

(65) Prior Publication Data
US 2009/0001853 A1    Jan. 1, 2009

Related U.S. Application Data

(63) Continuation of application No. PCT/JP2007/052097, filed on Feb. 7, 2007.

(30) Foreign Application Priority Data
Mar. 3, 2006    (JP)    ............................... 2006-057122

(51) Int. Cl.
*H01L 41/04*    (2006.01)
*H02N 1/00*    (2006.01)

(52) U.S. Cl. ....................... 310/322; 310/309; 310/317; 310/334

(58) Field of Classification Search ................. 310/322, 310/334, 317, 323.19, 335
See application file for complete search history.

(56) References Cited

U.S. PATENT DOCUMENTS 6,069,698 A *   5/2000   Ozawa et al. ............... 356/511
6,262,946 B1    7/2001   Khuri-Yakub et al.

(Continued)

FOREIGN PATENT DOCUMENTS

JP    H07-274287    10/1995

(Continued)

OTHER PUBLICATIONS

Itoh, T. "Onkyo Kogaku Genron" (vol. 1), 12$^{th}$ Edition, Kabushiki Kaisha CORONA sha, Dec. 10, 1980, p. 149-152.

(Continued)

*Primary Examiner*—Walter Benson
*Assistant Examiner*—Derek J Rosenau
(74) *Attorney, Agent, or Firm*—Scully, Scott, Murphy & Presser, P.C.

(57) ABSTRACT

An ultrasound transducer manufactured by using a micromachining process comprises: a first electrode into which a control signal for transmitting ultrasound is input; a substrate on which the first electrode is formed; a second electrode that is a ground electrode facing the first electrode with a prescribed space between the first and second electrodes; a membrane on which the second electrode is formed and which vibrates and generates the ultrasound when a voltage is applied between the first and second electrodes; a piezoelectric film contacting the membrane; and a third electrode electrically continuous to the piezoelectric film.

19 Claims, 14 Drawing Sheets

U.S. PATENT DOCUMENTS

| | | | |
|---|---|---|---|
| 6,328,696 | B1 | 12/2001 | Fraser |
| 6,328,697 | B1 | 12/2001 | Fraser |
| 6,836,159 | B2 | 12/2004 | Wodnicki |
| 6,865,140 | B2 | 3/2005 | Thomenius et al. |
| 2003/0011285 | A1* | 1/2003 | Ossmann ............... 310/334 |
| 2004/0267134 | A1* | 12/2004 | Hossack et al. ........... 600/459 |
| 2005/0162040 | A1* | 7/2005 | Robert .................. 310/322 |

FOREIGN PATENT DOCUMENTS

| | | |
|---|---|---|
| JP | 08-274573 | 10/1996 |
| JP | 2004-503313 | 2/2004 |
| JP | 2004-274756 | 9/2004 |
| JP | 2004-350705 | 12/2004 |
| WO | WO 01/97562 A3 | 12/2001 |

OTHER PUBLICATIONS

Akasheh, F., et al., "Piezoelectric Micromachined Ultrasonic Transducers: Modeling the Influence of Structural Parameters on Device Performance", IEEE Transactions on Ultrasonics, Ferroelectronics, and Frequency Control, Mar. 2005, vol. 52, No. 3, pp. 455-468.

Wang, Z., et al., "Fabrication and Characterization Piezoelectric Micromachined Ultrasonic Transducers with Thick Composite PZT Films", IEEE Transactions on Ultrasonics, Ferroelectronics, and Frequency Control, Dec. 2005, vol. 52, No. 12, pp. 2289-2297.

Guldiken, R., et al., "CMUTS with Dual-Electrode Structure for Improved Transmit and Receive Performance", IEEE Transactions on Ultrasonics, Ferroelectrics, and Frequency Control, Feb. 2006, vol. 53, No. 2, pp. 483-491.

* cited by examiner

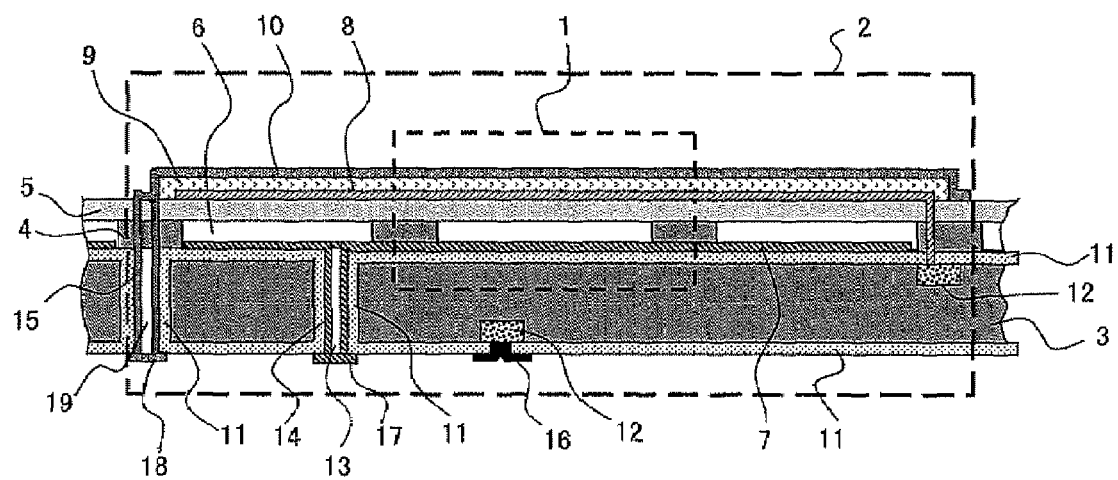
F I G. 1

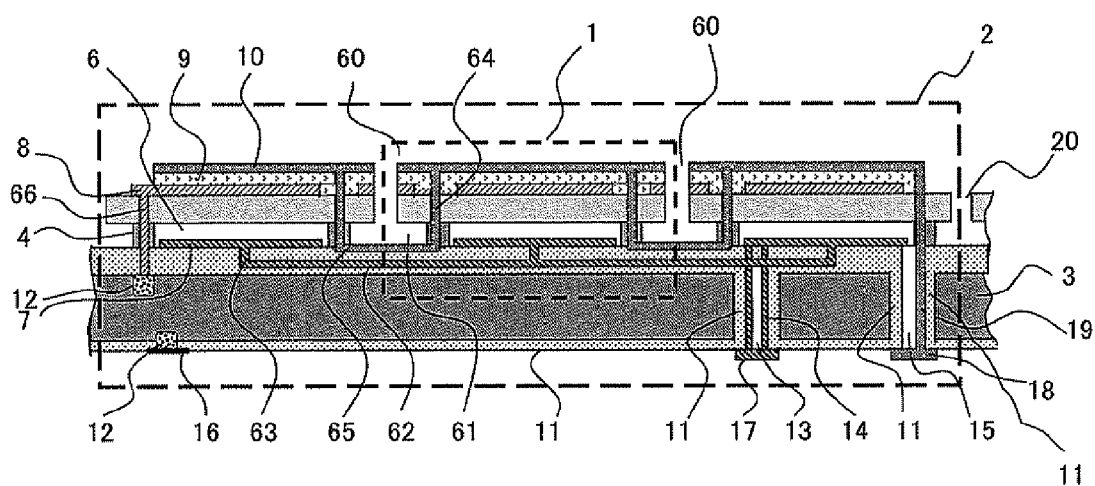
F I G. 5

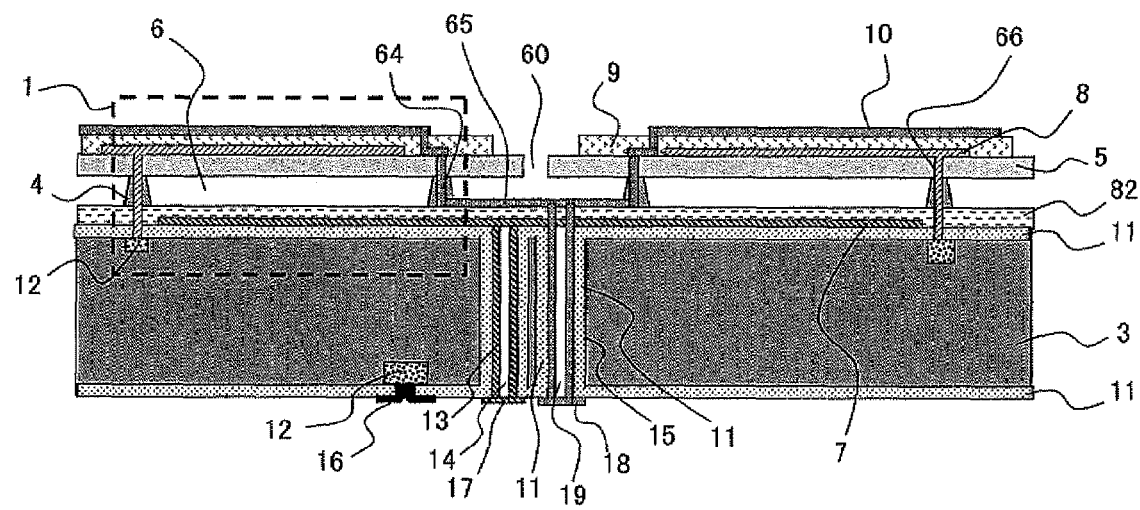
F I G. 7

FUNDAMENTAL
PIEZOELECTRIC
VIBRATION
($\lambda/2$ RESONANCE)

THIRD ORDER
PIEZOELECTRIC
VIBRATION
($3\lambda/2$ RESONANCE)

ULTRASOUND TRANSDUCER MANUFACTURED BY USING MICROMACHINING PROCESS, ITS DEVICE, ENDOSCOPIC ULTRASOUND DIAGNOSIS SYSTEM THEREOF, AND METHOD FOR CONTROLLING THE SAME

CROSS REFERENCE TO RELATED APPLICATIONS

This is a Continuation Application of PCT Application No. PCT/JP2007/052097, filed Feb. 7, 2007, which was not published under PCT Article 21 (2) in English.

This application is based upon and claims the benefit of priority from the prior Japanese Patent Application No. 2006-057122, filed Mar. 3, 2006, the entire contents of which are incorporated herein by reference.

BACKGROUND OF THE INVENTION

1. Field of the Invention

The present invention relates to a MUT (Micromachined Ultrasound Transducer).

2. Description of the Related Art

An ultrasound diagnosis method is commonly employed in which ultrasound is transmitted to walls of a body cavity and the state of the body cavity is converted into images on the basis of the echo signals thereof for the purpose of making diagnoses. An ultrasound endoscope is one of the devices used for this ultrasound diagnosis method.

The ultrasound endoscope has an ultrasound probe at the distal end of an insertion tube to be inserted into body cavities, and this ultrasound probe converts electric signals into ultrasound in order to transmit the ultrasound to body cavities and also receives ultrasound reflected in the body cavities in order to convert the received ultrasound into electric signals.

Conventionally, ceramic piezoelectric material PZT (lead zirconate titanate) has been used for piezoelectric elements that convert electric signals into ultrasound. However, micromachined ultrasound transducers (hereinafter, referred to as MUTs) have attracted attention. MUTs are among a category of devices that are referred to as micro electro-mechanical systems (MEMS).

Also, in recent years, capsule endoscopes have been realized that are swallowed into body cavities in order to obtain images of the body cavities (for example, Patent Document 8). By using this ultrasound diagnosis medical capsule endoscope, it is possible to make ultrasound diagnoses at sites at which it was previously difficult to make diagnoses.

Because the conventional MUTs have been configured to have membranes of respective transducer cells that are continuous along the plane direction, the continuous configuration has interfered with the deformation of the membranes of the respective transducer cells and the transverse waves have leaked to the adjacent transducer cells, and thereby the efficiency of the electromechanical conversion has been reduced.

Also, the membranes have been supported by the peripheral portions, and accordingly the bending vibrations of the membranes have leaked to the supporting members as longitudinal vibrations so that the mechanical quality factor Q has been reduced and the amplitude of the membrane has been small. Thereby, the S/N ratio has been reduced so that ultrasound diagnosis images have been deteriorated. Also, the conventional MUTs, especially cMUTs (capacitive micromachined ultrasound transducers) have required DC bias for both the reception and the transmission, and accordingly a driving control method that uses as small an amount of DC bias voltage as possible has been important. This DC bias has had to be applied for far longer periods of time for the reception than for the transmission, and thus a configuration that realizes reception without DC bias has been desired.

Also, the techniques relating to the present invention are disclosed in, for example, patent documents 1 through 8 below.

Patent Document 1:

Japanese Patent Application Publication No. H07-274287

Patent Document 2:

Japanese Patent Application Publication No. H08-274573

Patent Document 3:

Japanese Patent Application Publication No. 2004-274756

Patent Document 4:

U.S. Pat. No. 6,262,946

Patent Document 5:

U.S. Pat. No. 6,328,696

Patent Document 6:

U.S. Pat. No. 6,328,697

Patent Document 7:

Publication in Japan of translation of PCT International Patent Application No. 2004-503313 (WO 2001/097562)

Patent Document 8:

Japanese Patent Application Publication No. 2004-350705

Non-Patent Document 1:

Pages 149 through 152 in the Twelfth version of Volume 1 of "Onkyo Kogaku Genron" written by Tsuyoshi Itoh and published by CORONA PUBLISHING CO., LTD, in Dec. 10, 1980

SUMMARY OF THE INVENTION

An ultrasound transducer manufactured by using a micromachining process according to the present invention comprises:

a first electrode into which a control signal for transmitting ultrasound is input;

a substrate on which the first electrode is formed;

a second electrode that is a ground electrode facing the first electrode with a prescribed space between the first and second electrodes;

a membrane on which the second electrode is formed and which vibrates and generates the ultrasound when voltage is applied between the first and second electrodes;

a piezoelectric film contacting the membrane; and a third electrode jointed to the piezoelectric film.

An ultrasound transducer device according to the present invention is an ultrasound transducer device manufactured by using a micromachining process having an ultrasound transducer comprising:

a first electrode into which a control signal for transmitting ultrasound is input;

a substrate on which the first electrode is formed;

a second electrode that is a ground electrode facing the first electrode with a prescribed space between the first and second electrodes;

a membrane on which the second electrode is formed and which vibrates and generates the ultrasound when voltage is applied between the first and second electrodes;

a first piezoelectric film formed on the second electrode formed on a surface of the membrane; and a third electrode that is connected to the first piezoelectric film and faces the second electrode via the piezoelectric film, said ultrasound transducer device comprising:

a conversion unit boosting an alternating current low-voltage signal conveyed from a conveying cable, and converting it into a direct current voltage signal;

a first switching unit switching an electrical connection between the conversion unit and the first electrode;

a self oscillating unit performing self-oscillation on the basis of the direct current voltage signal input into the first electrode in order to drive the ultrasound transducer to transmit ultrasound;

a reception signal processing unit performing a prescribed signal process on a reception signal based on the ultrasound received by the ultrasound transducer; and a second switching unit switching an electrical connection between the conversion unit and the reception signal processing unit.

A method of controlling an ultrasound transducer according to the present invention is a method of controlling an ultrasound transducer manufactured by using a micromachining process, comprising:

a first electrode into which a control signal for transmitting ultrasound is input;

a substrate on which the first electrode is formed;

a second electrode that is a ground electrode facing the first electrode with a prescribed space between the first and second electrodes;

a membrane on which the second electrode is formed and which vibrates and generates the ultrasound when voltage is applied between the first and second electrodes;

a first piezoelectric film formed on the second electrode formed on a surface of the membrane; and a third electrode contacting the first piezoelectric film and facing the second electrode via the piezoelectric film, wherein:

the piezoelectric film stacked and arranged on a surface of the membrane detects deformation of the membrane that deforms corresponding to the control signal input into the first electrode.

A method of controlling an ultrasound transducer device according to the present invention is a method of controlling an ultrasound transducer device manufactured by using a micromachining process, comprising:

an ultrasound transducer including:
  a first electrode into which a control signal for transmitting ultrasound is input;
  a substrate on which the first electrode is formed;
  a second electrode that is a ground electrode facing the first electrode with a prescribed space between the first and second electrodes;
  a membrane on which the second electrode is formed and which vibrates and generates ultrasound when voltage is applied between the first and second electrodes;
  a first piezoelectric film formed on the second electrode formed on a surface of the membrane; and
  a third electrode connected to the first piezoelectric film and facing the second electrode via the piezoelectric film; and a conversion unit boosting an alternating current low voltage signal conveyed from a conveying cable, and converting it into a direct current voltage signal;

a first switching unit switching an electrical connection between the conversion unit and the bottom electrode;

a self oscillating unit performing self-oscillation on the basis of the direct current voltage signal input into the first electrode in order to drive the ultrasound transducer to transmit ultrasound;

a reception signal processing unit performing a prescribed signal process on a reception signal created on the basis of the ultrasound received by the ultrasound transducer; and a second switching unit switching an electrical connection between the conversion unit and the reception signal processing unit, wherein:

when transmitting ultrasound, the first switching unit is turned on and the second switching unit is turned off;

an alternating current voltage signal for controlling vibration of the membrane is boosted by the conversion unit in order to convert it into a direct current voltage signal;

the direct current voltage signal is supplied to the self oscillating unit via the first switching unit; and ultrasound is transmitted from the ultrasound vibration on the basis of the self oscillating unit.

BRIEF DESCRIPTION OF THE DRAWINGS

FIG. 1 is a cross-sectional view of a MUT element according to the first embodiment;

FIG. 5 shows a cross section of a MUT according to the second embodiment;

FIG. 7 shows a cross section of a MUT according to the fourth embodiment;

DESCRIPTION OF THE PREFERRED EMBODIMENTS

Figure 2:
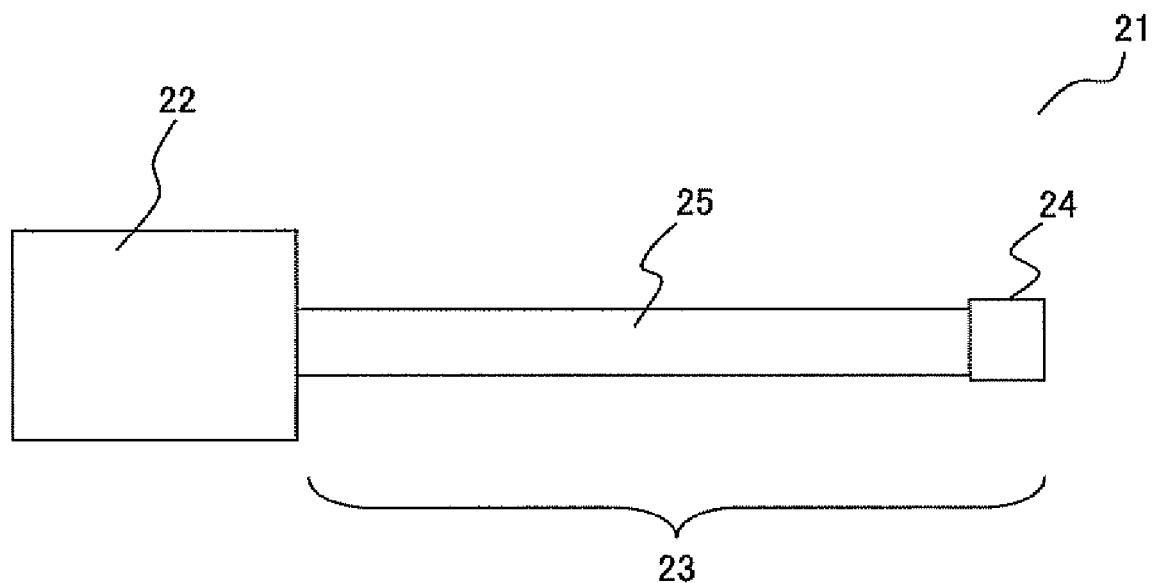
FIG. 2 schematically shows a configuration of an Endoscopic ultrasound diagnosis system that uses the MUT according to the first embodiment.

Conventionally, there has been no MUT having a configuration in which a cMUT and a pMUT (piezoelectric micromachined ultrasound transducer) are combined for one and the same ultrasound transducer cell.

By combining the cMUT and pMUT, the synergistic effects between the electrostatic forces of the cMUT and the piezoelectric effect of the pMUT increase the output of the ultrasound to be transmitted, and also increase the sensitivity for receiving the ultrasound.

It is an object of the present invention to provide an ultrasound transducer in which a cMUT and a pMUT are combined.

The ultrasound transducer according to the present invention is a device in which a substrate, a first electrode (bottom electrode that will be described later) formed thereon, a supporting member for supporting a membrane, and a second electrode (common ground electrode that will be described later) are stacked and arranged, and a lot of ultrasound transducer cells, including a membrane that vibrates with alternating current, are applied to both of the electrodes and transmit ultrasound in a forward direction.

Also, this ultrasound transducer is a device in which a piezoelectric film and electrodes (upper electrode that will be described later) for controlling signals are stacked and arranged on both of the surfaces of the piezoelectric film at a position close to the membrane.

By this configuration, it is possible to increase the output of the ultrasound to be transmitted and to increase the sensitivity for receiving ultrasound by using the electromotive force via the electrostatic force of the cMUT and the piezoelectric effect of the pMUT. Also, because the pMUT is used for the reception, there is the advantage that a DC bias voltage is not necessary. Hereinafter, the respective embodiments of the present invention will be explained.

First Embodiment

In the present embodiment, in an ultrasound transducer that is manufactured by using the micromachining process, a MUT for transmitting ultrasound by using the electrostatic force caused between the electrodes and the piezoelectric effect by the force activated in the piezoelectric film will be explained.

FIG. 1 is a cross-sectional view of a MUT element according to the present embodiment. The MUT element shown in FIG. 1 is a transducer that is the minimum unit to be controlled with the same phase and the same driving voltage, and is a micromachined ultrasound transducer consisting of a plurality of MUT cells 1.

A MUT element 2 includes a semiconductor substrate 3, supporting members 4, a membrane 5, cavities 6, a bottom electrode 7, a common ground electrode 8, a piezoelectric film 9, an upper electrode 10, an insulation film 11, a diffusion layer 12, through holes 13 and 19, a through hole wire 14 which is formed on the side wall of the through hole 13 and is electrically continuous to the bottom electrode 7, a through hole wire 15 which is formed on the side wall of the through hole 19 and electrically continuous to the upper electrode 10 formed on the piezoelectric film 9, a ground electrode pad 16, a bottom electrode pad 17 of the bottom electrode 7, and a upper electrode pad 18 of the upper electrode 10 formed on the piezoelectric film 9.

In the MUT element 2, the surface of the substrate 3 (Si substrate) is covered by an oxide film ($SiO_2$) (insulation film 11). In each cell 1, the supporting members 4 disposed at both ends of the cell 1 support the membrane 5. The supporting member 4 is formed of an insulation body made of SiN, $SiO_2$, or the like. The membrane 5 is made of SiN.

The bottom electrode 7 is disposed on the upper surface of the substrate 3 between the supporting members 4. In FIG. 1, the cavities 6 are spaces enclosed by the supporting members 4 and the bottom electrode 7. A dielectric film may be formed on the bottom electrode 7, and in this case, the cavities 6 are spaces enclosed by the membrane 5 and the supporting members 4.

The through hole 13 pierces the substrate 3. The side wall of the through hole 13 has the insulation film 11 on its surface, and the through hole wire 14 is formed on the insulation film 11. The through hole wire 14 is electrically continuous to the bottom electrode 7 and the bottom electrode pad 17 formed on the bottom surface of the bottom electrode 7. In other words, the bottom electrode pad 17 serves as a terminal on the bottom surface side of the substrate 3 with respect to the bottom electrode 7.

The common ground electrode 8 is formed on the upper surface of the membrane 5, and the piezoelectric film 9 is formed thereon. The common ground electrode 8 is connected with the diffusion layer 12 formed on the upper surface of the substrate 3. Also, the diffusion layer 12 is formed on the bottom surface of the substrate 3 in order to realize the ohmic contact.

By providing the diffusion layer 12, it is possible to reduce, to an extreme level, the direct current resistance between the upper surface of the low-resistive semiconductor substrate 3 and the diffusion layer 12 of the bottom surface side. The diffusion layer 12 on the bottom surface side of the substrate 3 is electrically continuous to the ground electrode pad 16. Accordingly, the ground electrode pad 16 serves as a terminal on the bottom surface side of the substrate 3 with respect to the common ground electrode 8.

The material of the piezoelectric film 9 desirably does not contain lead. The piezoelectric film 9 is made of, for example, aluminum nitride, zinc oxide, barium titanate, barium strontium titanate, or the like. The piezoelectric characteristic that is required for the piezoelectric film used in the present embodiment is $g_{33}$ in terms of the voltage output coefficient, and any material can be used for the piezoelectric film as long as that material does not contain lead and yields relatively high $g_{33}$.

On the upper surface of the piezoelectric film 9, the upper electrode 10 is formed. The through hole 19 pierces the substrate 3. The insulation film 11 is formed on the side wall of the through hole 19, and the through hole wire 15 is formed thereon. The through hole wire 15 is electrically continuous to the upper electrode pad 18 provided on the bottom surface of the substrate 3. The upper electrode 10 is electrically continuous to the through hole wire 15. In other words, the upper electrode pad 18 serves as a terminal corresponding to the upper electrode 10 on the bottom surface side of the substrate 3.

The MUT shown in FIG. 1 has a configuration in which the common ground electrode 8, one of the electrodes formed on both sides of the piezoelectric film 9 for controlling signals, shares it with the upper of the membrane as an electrode. In other words, the MUT shown in FIG. 1 has a configuration in which the cMUT and the pMUT (piezoelectric element formed on the membrane) are combined.

Next, the operations of the MUT shown in FIG. 1 will be explained by referring to FIGS. 2 and 3.

FIG. 2 schematically shows the configuration of an Endoscopic ultrasound diagnosis system that uses the MUT according to the present embodiment. An Endoscopic ultrasound diagnosis system 21 includes the insertion tube 23 and an observation device 22.

The insertion tube 23 is in the shape of a long and narrow tube in order to be inserted into body cavities. The insertion tube 23 includes, from the distal end, an ultrasound probe 24, a bending section, and a flexible tube section 25. The ultrasound probe 24 includes the MUT shown in FIG. 1, and transmits and receives ultrasound signals. The bending section is a section that is disposed at the distal end of the ultrasound probe 24 and that can bend arbitrarily. The flexible tube section is disposed at the distal end of the bending section, is narrow, long, and flexible. In the bending section and the flexible tube section 25, there are coaxial cables.

The observation device 22 generates control signals for turning on and off a switch (SW) in the ultrasound probe 24, outputs a low-voltage AC, and performs a signal process on the signals from the ultrasound probe 24 in order to convert the signals into image signals.

Figure 3:
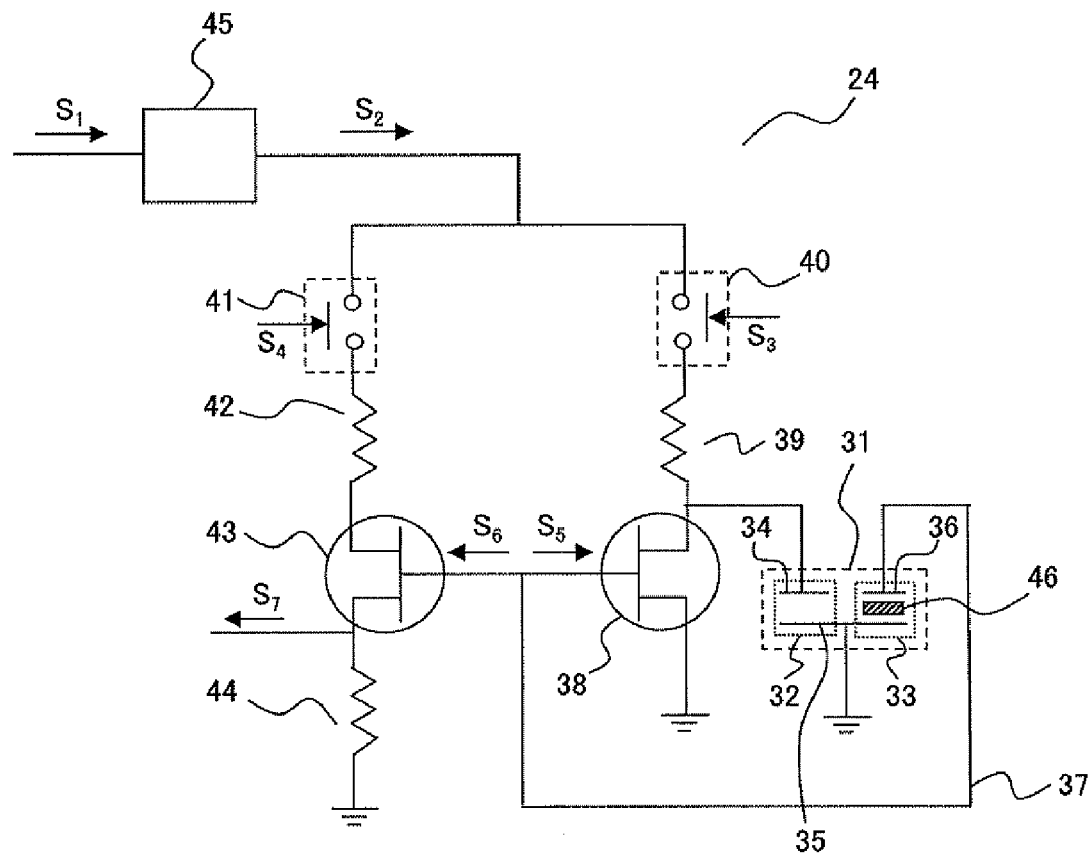
FIG. 3 shows a circuit configuration of an ultrasound probe 24 according to the first embodiment.

FIG. 3 shows a circuit configuration of the ultrasound probe 24 according to the present embodiment. The ultrasound probe 24 includes a MUT 31, FETs (field effect transistors) 38 and 43, resistors 39, 42, and 44, switches (SWs) 40 and 41, and an AC-DC converter 45.

The MUT 31 corresponds to the MUT shown in FIG. 1, and its configuration corresponds to the combination of the cMUT 32 and the pMUT 33. The cMUT 32 and the pMUT 33 have a common ground electrode 35.

The cMUT 32 includes a bottom electrode 34 and the common ground electrode 35. The cMUT 32 corresponds to a portion including the bottom electrode 7, the cavity 6, and the common ground electrode 8 shown in FIG. 1.

The pMUT 33 includes the upper electrode 36, the piezoelectric film 46, and the common ground electrode 35. The pMUT 33 corresponds to a portion including the upper electrode 10, the piezoelectric film 9, and the common ground electrode 8 shown in FIG. 1.

A switch control signal generator (not shown) generates control signals for turning on/off the SWs 40 and 41. In other words, the switch control signal generator generates signals for determining timings at which the SWs 40 and 41 are turned on and off, and time periods during which they are in the on or off states. The SWs 40 and 41 are a pair of electronic switches that are in a reverse relationship to each other with respect to time.

Also, a self oscillating circuit is made of the MUT 31, the FET 38, and a transmission line 37 for returning a signal (signal feedback) from the MUT 31 to FET 38.

Next, the transmission and the reception of ultrasound beams of the cell 1 according to the present embodiment will be explained.

When transmitting ultrasound beams, the switch control signal generator (not shown) that has received a control signal from the observation device 22 performs controls so that the switch SW40 is turned on on the basis of the SW control signal $S_3$ and that the switch SW41 is turned off on the basis of the SW control signal $S_4$.

An AC signal (alternating voltage signal) $S_1$ is transmitted from the control signal 22 via coaxial cables in the insertion tube 23, and is input into the AC-DC converter 45. The AC-DC converter 45 boosts the AC signal by using a micromachined voltage trans or the like, converts that boosted AC signal into a DC signal, and further boosts it in order to output a DC voltage signal (direct current high-voltage signal) $S_2$.

The DC voltage $S_2$ is applied to the bottom electrode 34 of the cMUT 32 via the SW40 and the resistor 39. Thereby, the electrostatic force that is excessively caused between the bottom electrode 34 and the common ground electrode 35 excessively deforms the membrane 5.

Accompanying the excessive deformation of the membrane 5, the piezoelectric film 46 provided on the upper surface of the membrane 5 excessively deforms, too. Thereby, the deformation of the piezoelectric film 46 is converted into voltage signals by the piezoelectric effect. The voltage signal obtained by the conversion is input into a gate (G) of the FET 38 as the feedback signal $S_5$ through the transmission line 37. This voltage signal is of a very low voltage compared with the driving signal so that this signal will not cause any problem with respect to security even when this signal is caused on the side of the electrode contacting the living body.

When the feedback signal $S_5$ is input into the gate (G) of the FET 38, the resistance between the drain (D) and the source (S) of the FET 38 decreases so that the voltage applied to the bottom electrode 34 of the cMUT 32 is lowered. Thereby, the voltage applied to the membrane 5 of the cMUT 32 is also lowered and the force applied to the piezoelectric film 46 of the pMUT 33 side is removed, and accordingly the piezoelectric signal based on the piezoelectric voltage of the pMUT 33 is not caused, and thereby the feedback signal $S_5$ is not output from the upper electrode 36. Accordingly, the gate voltage of the FET 38 becomes zero, and the resistance between the drain and the source increases so that a high voltage close to the DC voltage signal $S_2$ is again applied to the bottom electrode 34 of the cMUT 32. This phenomenon is repeated during the transmission of ultrasound. This repeating frequency is equal to the resonance frequency of the membrane, and this self-oscillation continues as long as the DC voltage $S_2$ is supplied to the FET 38.

As described above, the piezoelectric film 9 that is stacked and arranged on the membrane 5 causes a voltage based on the piezoelectric effect in accordance with the deformation of the membrane 5. In other words, the piezoelectric film 9 is used to detect the deformation of the membrane 5.

Thereby, the self oscillating circuit can obtain the resonance frequency by causing positive feeding back of the feedback signal during the transmission of ultrasound. Accordingly, the vibration of the MUT becomes stabilized at the resonance frequency. As a result of the vibration of the membrane caused by this vibration operation, ultrasound is generated and transmitted toward the upper direction of the upper electrode 36.

Next, when receiving ultrasound, the switch control signal generator (not shown) that has received a control signal from the observation device 22 performs control so that the switch SW40 is turned off on the basis of the SW control signal endoscopic ultrasound diagnosis system and the switch SW41 is turned on on the basis of the SW control signal $S_4$.

When the MUT 31 has received an ultrasound beam, the piezoelectric film 46 of the pMUT 33, converts ultrasound beams into electric signals (pulse echo signals $S_6$) by the piezoelectric effect. The pulse echo signal $S_6$ is input into the gate (G) of the FET 43. Thereby, the pulse echo signal $S_6$ is amplified, is output from the source (S) side of the FET 43, and is output as a pulse echo signal $S_7$ to the observation device 22 via the coaxial cable.

The FET 43 has a function of amplifying pulse echo signals, a function of performing the impedance conversion (converting high impedance into low impedance), and a function of detecting charges on the surfaces of the electrodes of the MUT 31. The function of detecting charges is a function of detecting the charges that are changed by the piezoelectric effect of the pMUT 33 caused by the vibration of the membrane in accordance with the reception strength of the wave received by the MUT 31, said wave being ultrasound transmitted from the membrane surface of the MUT 31 and being reflected in the body cavities.

In the above explanation, the voltage signal obtained by the piezoelectric effect of the piezoelectric film at the time of receiving ultrasound is a pulse echo signal; however, by obtaining the charges that can be obtained in the upper electrode (the common ground electrode 35 in FIG. 3) of the cMUT and detecting them together with the voltage that can be obtained by the piezoelectric film similarly as in the conventional techniques, it is possible to increase the reception sensitivity.

Also, the phases are shifted respectively by $\pi$ (total $2\pi$) in the FET 38 and the MUT 31 in the positive feedback loop including the MUT 31, the transmission line 37 and the FET 38. At that time, the phases are not shifted by $2\pi$ precisely, depending upon the circumstances; in other words, errors may be caused. In this case, in order to correct the errors, it is possible to adjust the phase by adding a phase adjustment element such as a resistor or the like on the transmission line 37. Also, the MUT 31 can be produced by using the micromachining process on Si substrates, and accordingly it is possible to form the FETs 38 and 43, the resistors 39, 42, and 44, the SWs 40 and 41, and the AC-DC convertor 45 on or in the Si substrates on which the MUT is formed. Thereby, it can be compact.

Figure 4:
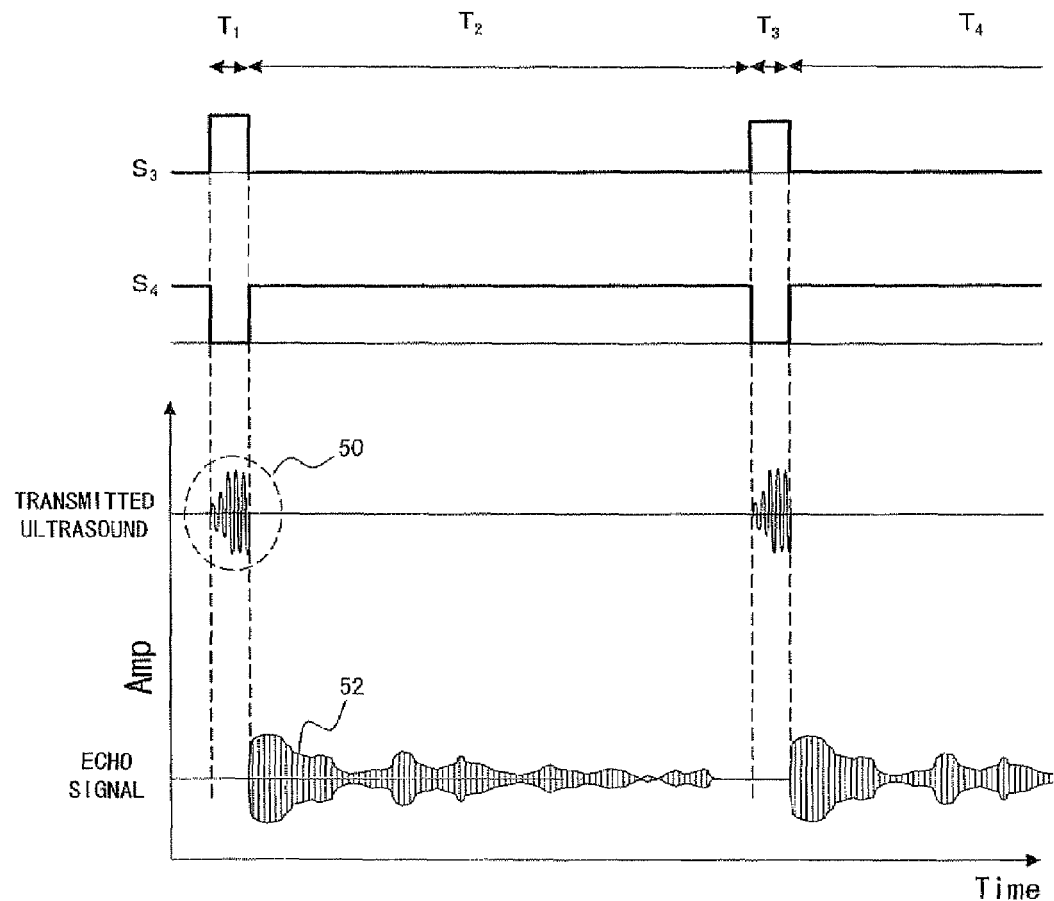
FIG. 4 is a timing chart of the operations for switch (SW) and of a driving voltage signal for transmitting an ultrasound wave according to the first embodiment.
Figure 4:
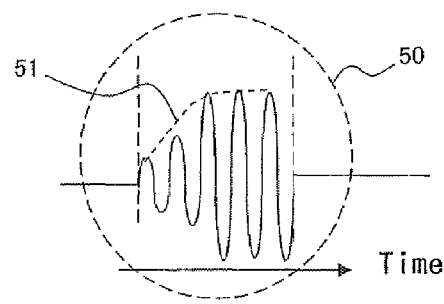

FIG. 4 is a timing chart of the operations for switch (SW) and of a driving voltage signal for transmitting the ultrasound wave according to the present embodiment. FIG. 4 will be explained by referring to FIG. 3. As shown in FIG. 4, accompanying the switching between the SW40 and SW41, the ultrasound wave transmission time periods ($T_1$, $T_3$, . . . ) and the echo signal reception time periods ($T_2$, $T_4$, . . . ) are repeated.

At the timing $T_1$, the SW40 is turned on on the basis of the SW control signal $S_3$ ($S_3$=ON), and the SW41 is turned off on the basis of the SW control signal $S_4$ ($S_4$=OFF). As explained in FIG. 3, ultrasound signals are output from the MUT 31. A waveform 50 represents a signal waveform of the ultrasound transmitted from the MUT 31. The lower figure of FIG. 4 is an enlarged view of the waveform 50. The waveform denoted by numeral 51 represents an envelope waveform that is tied the peak values of the amplitude waveform of the transmitted ultrasound.

Next, at the timing $T_2$, the SW40 is turned off on the basis of the SW control signal $S_3$ ($S_3$=OFF), and the SW41 is turned on on the basis of the SW control signal $S_4$ ($S_4$=ON). As explained in FIG. 3, the ultrasound is received by the MUT 31, and the ultrasound signal is converted into electric signals by the piezoelectric film 46. Numeral 52 denotes the waveform of the received echo signal.

Also, in FIG. 4, the scale of the amplitudes of the waveform 50 and the echo signal waveform 52 are expressed to the same extent for simplicity of explanation. However, the scale of the amplitude of the echo signal waveform 52 is actually rather small compared to the waveform 50.

According to the present embodiment, the ultrasound transducer manufactured by using the micromachining process has a first period (ultrasound transmission period) during which ultrasound is transmitted by applying an alternating current to a first electrode (bottom electrode 34) and a second electrode (common ground electrode 35), and a second period (echo signal reception period) during which voltage generated by the ultrasound reception between a third electrode (upper electrode 36) and the second electrode (common ground electrode 35) is conveyed to a reception signal processing circuit.

Also, the switching between the first and second periods is controlled by a pair of electronic switches SW40 and SW41 that are in a reverse relationship to each other with respect to time. This pair of the electronic switches can be integrated into the surface or inner of substrate 3 or be integrated in the substrate 3 by using the CMOS process.

Also, according to the present embodiment, the reception signal processing circuit includes a charge amplifier function, a voltage amplification function, and an impedance conversion function.

Also, the piezoelectric film stacked on the membrane can detect the deformation of the membrane.

Also, according to the present embodiment, the output of the ultrasound increases due to self-oscillation. The self-oscillation is autonomously set to be at a frequency at which the vibration system vibrates most efficiently by the feedback signals and the phase reverse amplification element (FET 38).

Also, according to the present embodiment, it is possible to perform control so that an excessive signal is applied to the first and second electrodes in order to activate the membrane; the activation signal is detected by the piezoelectric film; the detection signal is conveyed to the amplification element as the feedback signal; the amplification element, the piezoelectric element, and the phase adjustment element form a positive feedback loop; the membrane is caused to generate a self vibrated ultrasound; and the first period, during which the ultrasound is transmitted, and the second period, during which the voltage generated between the third and second electrodes by the ultrasound reception is conveyed to the reception signal processing circuit, are included.

Also, according to the present embodiment, it is possible to employ a configuration in which an amplification element (FET), a phase adjustment element, a reception signal processing circuit (FET or the like), and a pair of electronic switches are integrated on a silicon substrate.

Second Embodiment

In the present embodiment, a MUT that is obtained by adding, to the MUT according to the first embodiment, means for reducing a vibration loss will be explained. Also, in the explanation below, the same constituent elements as in the above embodiment are denoted by the same numerals; accordingly, for the detailed explanation thereof, to be referred to the above embodiment.

FIG. 5 shows a cross section of a MUT according to the present embodiment. The MUT shown in FIG. 5 is an ultrasound transducer that is manufactured by using the micromachining process. In the MUT shown in FIG. 5, the membranes between the cells are divided. The spaces between the adjacent cells are referred to as interstices 60.

Further, a bridge wire 65 between upper electrodes 10 of adjacent cells is provided on a bottom 61 of each interstice 60 so that the upper electrodes 10 of the adjacent cells are electrically continuous to each other through a via wire 64. Also, the respective bottom electrodes 7 of the respective cells are electrically continuous to each other by a bridge wire 62 between bottom electrodes of adjacent-cells through a via wire 63. Also, the wire 64 from the upper electrode 10 and the common ground electrode 8 are electrically insulated from each other by using the piezoelectric film 9 at the point at which they cross each other.

Also, in FIG. 5, the diffusion layer 12 is formed on the surface of the substrate 3. Also, from the electrode 8, a via hole piercing the membrane, the supporting member, and the insulation film 11 are formed, and a via wire 66 is formed along this via hole. The common ground electrode 8 is connected to the diffusion layer 12 through this via wire 66. Also, in the present example, the cells are divided accordingly, and the ground electrodes are also divided. Accordingly, the via wires have to be formed for each cell in FIG. 5; however, in order to simplify the illustration, they are not shown.

In the MUT according to the present embodiment, the supporting members 4 are formed along the nodes of the fundamental vibration obtained when the membrane 5 vibrates freely. For example, when the shape of the membrane 5 is a circle when viewed from above, the supporting members 4 are provided along a position 0.678a from the center of the circle of the membrane 5 if the radius of the circle of the same membrane 5 is a (a is an integer that can be selected arbitrarily). (non-Patent Document 1)

According to non-Patent Document 1, a circular plate whose periphery is free causes a diameter node line that is arranged at intervals equal to those of the node line of the concentric circle when vibrating. Especially when the shape is symmetric, which POISSON solved in 1829, and the minimum vibration thereof causes the node line at 0.678a (a is the radius of the circular plate), and the next behavior is caused at 0.392a and 0.842a.

As described above, because the membrane of each cell is not connected with the membrane of the next cell, the dissipation of the vibration toward the planar direction (adjacent membrane direction) is avoided. Also, the membrane is supported at the positions at which deformation due to the fundamental vibration is not caused, and accordingly it is possible to prevent the vibration from leaking to the semiconductor substrate as the longitudinal wave.

Also, this MUT can apply the circuit shown in FIG. 3 similarly to the first embodiment. Accordingly, it is possible to detect the deformation of the membrane 5, and to cause the self-oscillation in the positive feedback loop by using the detected signal as the feedback signal and also by using the piezoelectric film 9.

According to the present embodiment, the membrane of each cell is independent from the membranes of the adjacent cells so that it is possible to avoid the dissipation of the vibration toward the planar direction.

Also, according to the present invention, the membrane is supported at the parts of the nodes of the membrane that do not vibrate inherently so that the dissipation of the vibration of the membrane through the supporting members is reduced (in other words, the vibration loss of the membrane is reduced), and accordingly a high mechanical quality factor Q, i.e., a high vibration efficiency of the membrane (High Q), is obtained. As a result of this, the ultrasound transmission efficiency increases.

Also, according to the present embodiment, the vibration of the membrane does not leak via the supporting members so that it is possible to remedy the crosstalk phenomenon in which the vibrations that leaked through the supporting members become longitudinal waves and are reflected by the back plane of the silicon substrate, and the reflected waves are converted into the membrane vibration of the adjacent cell via the supporting members.

According to the present embodiment, by using the self oscillating circuit, it is possible to stabilize the vibration of the MUT at the resonance frequency. Also, the MUT can be manufactured on a Si substrate by using a micromachining process; accordingly it is possible to form the FETs 38 and 43, the resistors 39, 42, and 44, SWs 40 and 41, and the AC-DC convertor 45 on or in the Si substrate in which the MUT is formed. Accordingly, it can be made to be further more compact.

Third Embodiment

In the present embodiment, a MUT having a filtering function by which high-frequency components can be removed is explained. In the explanations below, the same constituent elements as in the above explanations are denoted by the same numerals; accordingly, refer to the above explanations for the detailed explanation thereof.

Figure 6:
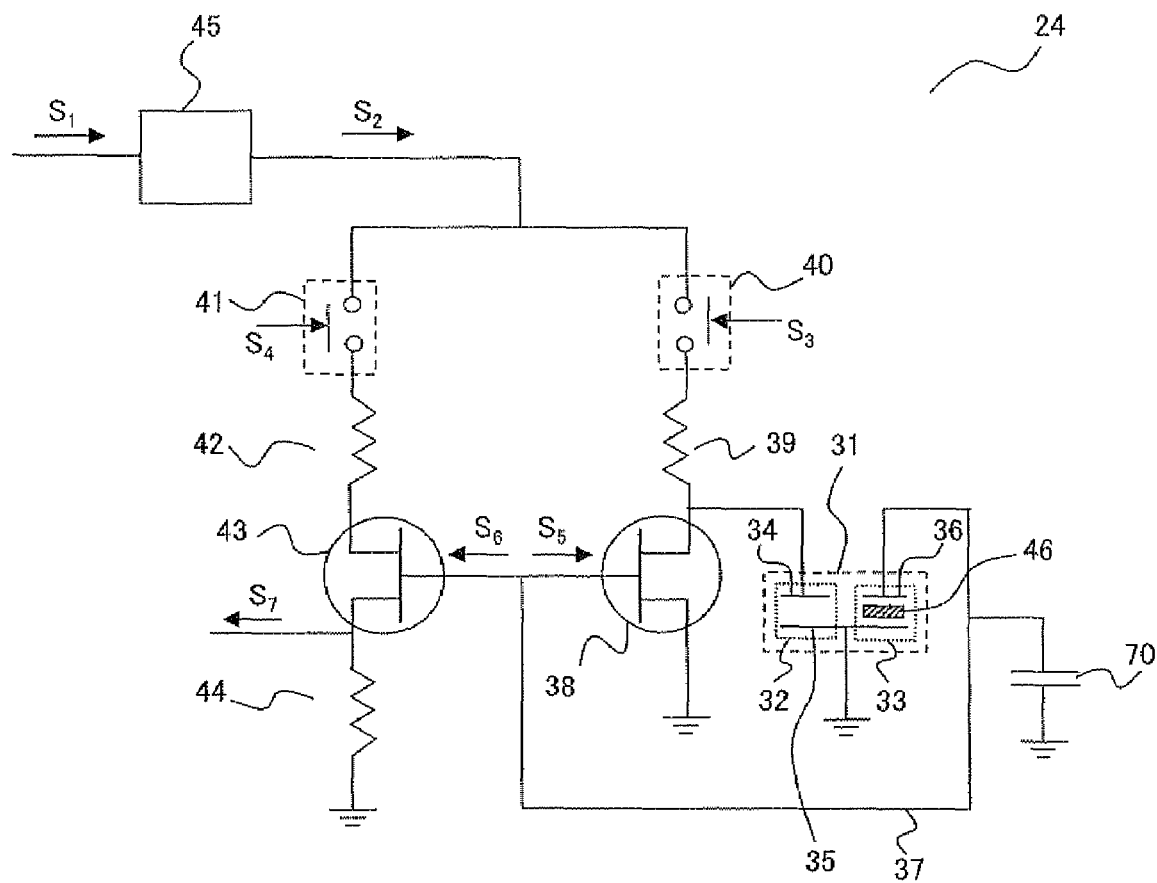
FIG. 6 shows a circuit configuration of the ultrasound probe 24 according to the third embodiment.

FIG. 6 shows a circuit configuration of the ultrasound probe 24 according to the present embodiment. FIG. 6 is obtained by adding a capacitor 70 to the circuit shown FIG. 3. One of the terminals of the capacitor 70 is connected to the transmission line 37, and the other terminal is grounded. By the capacitor 70, high-frequency components of the feedback signal $S_5$ can be removed.

The high-frequency components to be removed are the high frequency waves corresponding to the high-order vibration mode. This type of high frequency wave can be removed by adjusting the capacitance of the capacitor 70. As a result of the removal of the high-frequency waves, it is possible to generate the fundamental vibration only of the fundamental frequency mode.

The increase of the driving voltage at the moment when the SW 40 is first turned on is a step signal having a time constant that is determined by the resistor 39 and the capacitance of the cMUT 32, and is a wide band signal. Accordingly the high-order wave vibrations tend to be caused together with the fundamental vibration on the membrane. Accordingly, it is necessary to increase the efficiency of the desired fundamental wave vibrations by removing the waves that are not necessarily fundamental waves.

According to the present embodiment, it is possible to generate only the fundamental vibration by removing the high-frequency wave components that causes high-order vibrations. Thereby, extra vibrations are not generated and thus the vibration efficiency increases. Also, the present embodiments can be applied to both the first and second embodiments.

Fourth Embodiment

In the present embodiment, a MUT that vibrates only at the fundamental vibration mode among a plurality of vibration modes will be explained. Specifically, in the present embodiment, a MUT that generates only the fundamental vibrations and does not generate a high-order vibration mode itself will be explained. In the explanation below, the same constituent elements as in the above embodiments are denoted by the same numerals; accordingly, refer to the above embodiments for the detailed explanation thereof.

FIG. 7 shows a cross section of the MUT according to the present embodiment. The MUT shown in FIG. 7 is an ultrasound transducer that is manufactured by using a micromachining process. In FIG. 7, the MUT includes the semiconductor substrates 3, the supporting members 4, the membranes 5, the cavities 6, the bottom electrode 7, the common ground electrode 8, the piezoelectric films 9, the upper electrodes 10, the insulation films 11, the diffusion layers 12, the through holes 13 and 19, the through hole wire 14, the through hole wire 15, the ground electrode pad 16, the bottom electrode pad 17, the upper electrode pad 18, the via wires 64 and 66, the bridge wire 65, and an insulation film 82.

In the MUT element 2, the surface of the substrate (Si substrate) 3 is covered with an oxide film (SiO$_2$) (insulation film 11). In each cell 1, the membrane 5 is supported by the supporting members 4 disposed at both ends of each cell 1. The supporting members 4 are made of SiN or SiO$_2$. The membrane 5 is made of SiN.

On the surface of the substrate 3 between the supporting members 4, the bottom electrode 7 is formed. On the bottom electrode 7, the insulation film 82 is formed. The cavity 6 is enclosed by the membrane 5, the supporting member 4, and the insulation film 82.

The through hole 13 pierces the substrate 3. On the side wall of the through hole 13, the through hole wire 14 is formed. The through hole wire 14 electrically connects the bottom electrode 7 and the bottom electrode pad 17 provided on the bottom surface of the substrate 3. In other words, the bottom electrode pad 17 serves as a terminal of the bottom of the substrate 3 with respect to the bottom electrode 7.

The common ground electrode 8 is formed on the upper surface of the membrane 5. The piezoelectric film 9 is formed thereon. The common ground electrode 8 is electrically continuous to the diffusion layer 12 provided on the upper surface side of the substrate 3 through the via wire 66. Also, the diffusion layer 12 is provided on the bottom surface side of the substrate 3. The upper surface side and the bottom surface side of the substrate 3 are electrically continuous to each other through the diffusion layer 12. The diffusion layer 12 on the bottom surface side of the substrate 3 is electrically continuous to the ground electrode pad 16. Accordingly, the ground electrode pad 16 serves as a terminal of the bottom surface side of the substrate 3 with respect to the common ground electrode 8.

The material of the piezoelectric film 9 does not contain lead. The piezoelectric film 9 is made of, for example, aluminum nitride, zinc oxide, barium titanate, barium strontium titanate, or the like.

On the upper surface of the piezoelectric film 9, the upper electrode 10 is formed. The via wire 64 is provided to the upper electrode 10 of each cell, and they are electrically continuous through the bridge wire 65.

The through hole 19 pierces the substrate 3. On the side wall of the through hole 19, the through hole wire 15 is formed. The through hole wire 15 is electrically continuous to the upper electrode pad 18 provided on the bottom surface of the substrate 3. The upper electrode 10 is electrically continuous to the through hole wire 15. In other words, the upper electrode pad 18 serves as a terminal of the bottom surface side of the substrate 3 with respect to the upper electrode 10.

The membrane 5 of each cell according to the present embodiment is separated from the membranes of the adjacent cells by the interstices 60, and is independent. Also, the MUT according to the present embodiment has the supporting members 4 along the nodes of the fundamental vibrations obtained when the membranes 5 vibrate freely.

For the insulation film 82, materials having a high dielectric constant such as SrTiO$_3$, barium titanate BaTiO$_3$, barium strontium titanate, tantalum pentoxide, niobium oxide stabilized tantalum pentoxide, oxidized aluminum, oxidized titanium TiO$_2$ or the like are used.

Figure 8:
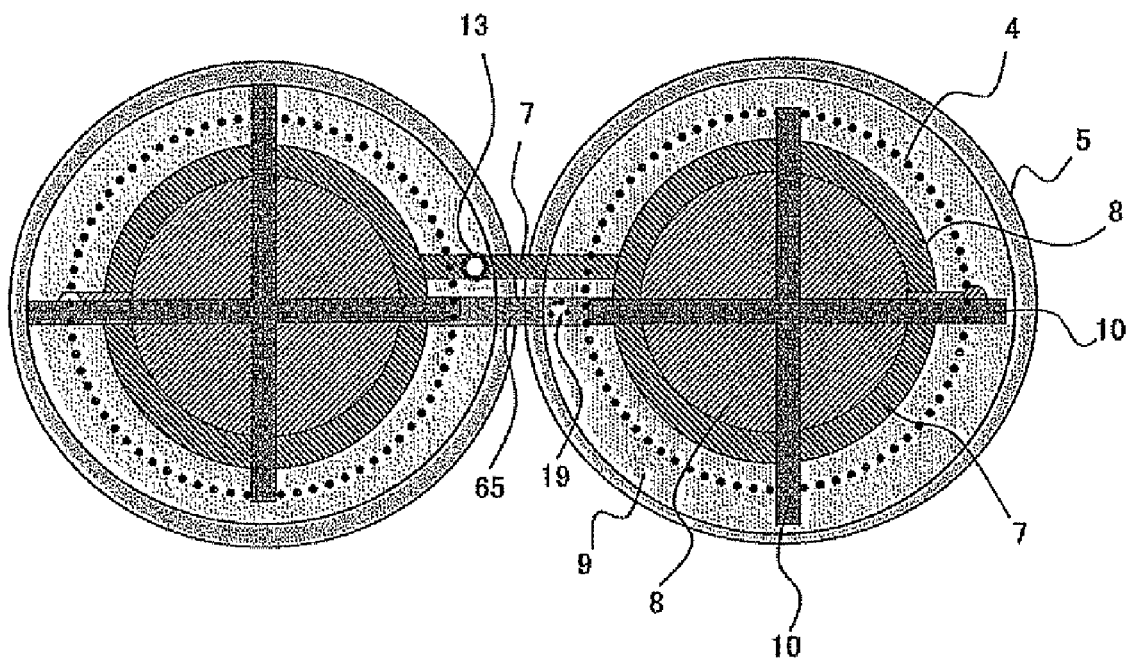
FIG. 8 is a top view of the MUT shown in FIG. 7.

FIG. 8 is a top view of the MUT shown in FIG. 7. As shown in FIG. 8, the MUT according to the present embodiment does not form the upper electrode 10 entirely over the membrane 5, but forms it on parts (parts indicated by cross shapes in FIG. 8) thereof.

Figure 9A:
FIG. 9A shows the fundamental piezoelectric vibration in order to explain the principle of the MUT according to the fourth embodiment.
Figure 9B:
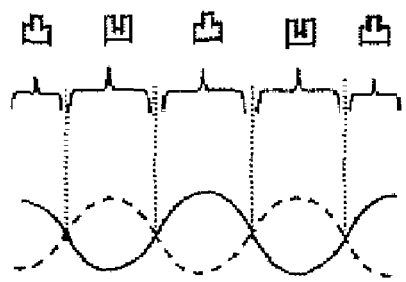
FIG. 9B shows the third order piezoelectric vibration in order to explain the principle of the MUT according to the fourth embodiment.

The high-frequency waves to be removed according to the present embodiment are only of the frequency that is obtained by multiplying the fundamental frequency with odd numbers (three times, five times . . . ). The vibration of the circular plate resonates with not only the fundamental waves but also with the frequency obtained by multiplying the odd numbers. The nodes of the vibrations are different from those of the fundamental waves. When the piezoelectric film causes the bending vibrations, it becomes convex or concave in the same direction over its entirety in the case of the fundamental waves, and accordingly the polarity of the voltage charge generated in the electrode is the same (see FIG. 9A). However, in the piezoelectric high-order vibration, the directions of the convexities are opposed to each other between the inside and the outside of the node when it is the third order. Accordingly, the generated charges are also opposed (see FIG. 9B).

When one electrode receives these charges of both polarities, the charges are cancelled in the electrode, and at the same time this piezoelectric high-order vibration is damped. If a feedback signal including the piezoelectric high-order vibration is used, a frequency-changing phenomenon (in which the fundamental vibration changes into the high-order piezoelectric vibrations depending upon the circumstances) is caused, and the vibration becomes unstabilized so that the vibration efficiency is reduced and a malfunction occurs. Above phenomena sometimes called as resonant frequency jump phenomena. For example, the node of the fundamental wave having a $\lambda/2$ resonance and the node of the high-order vibration having a $3\lambda/2$ resonance are close to each other, and accordingly $3\lambda/2$ resonances tend to be generated, and the charges of the opposed polarity generated by this $3\lambda/2$ resonance are short-circuited in the electrode so that only the charges generated by the fundamental vibrations remaining as a result are used as the feedback signals.

Also, in FIG. 8, one end of the upper electrode 10 is not extended to the end of the membrane 5; however, the scope of the present invention is not limited to this example, and it may be extended to the outer periphery of the membrane 5. Also, the length of the upper electrode 10 may be equal to the radius in an extreme case (one end of the upper electrode 10 has to be extended to the periphery of the membrane, and the other end has to pass through the center of the membrane).

Also, the scope of the present invention is not limited to the cross shape composed of two lines in FIG. 8, and one or three or more lines can be used. Also, the shape is not limited to being linear, and circles or the like can be used.

Also, the MUT shown in FIG. 8 can be used for the circuit shown in FIG. 3. However, in this case, it is not suitable for the left portion of the circuit (mechanical portion for the echo signal reception). When it is to be applied to the left portion in FIG. 3, the upper electrode 10 of the piezoelectric film 9 would more suitably be circular rather than being the cross shape electrode so that it can be closer to the diameter of the piezoelectric film because piezoelectric conversion signals (charge signals) from the ultrasound echo signals can be obtained in greater number, and this is advantageous.

In the third embodiment, the high-frequency wave components are removed by the control of the circuit. However, in the present embodiment, only the fundamental vibrations are generated and high-order vibrations are not generated so that the high-frequency wave components themselves are not caused.

Fifth Embodiment

In the present embodiment, a MUT that uses the piezoelectric elements for the supporting members is explained. Also, in the explanation below, the same constituent elements as in the above embodiments are denoted by the same numerals, and for the detailed explanation thereof, refer to the above embodiments.

Figure 10:
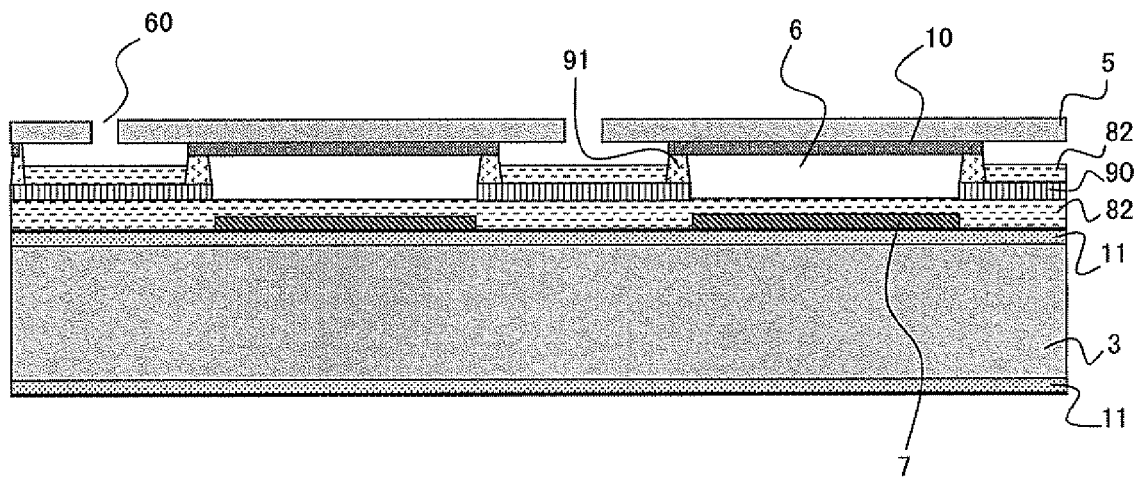
FIG. 10 shows a cross section of the MUT according to the fifth embodiment.

FIG. 10 shows a cross section of the MUT according to the present embodiment. The MUT shown in FIG. 10 is a micro-machined ultrasound transducer. The MUT includes the semiconductor substrate 3, piezoelectric supporting members 91, the membranes 5, the cavities 6, the bottom electrodes 7, the upper electrodes 10, the insulation film 11, the insulation film 82, and drive electrodes 90 for driving a piezoelectric supporting member 91. Also, in FIG. 10, the diffusion layer, the substrate through hole, the through hole wire which is formed on the side wall of the through hole and is electrically continuous to the bottom electrode, and the like are not shown.

The surface of the substrate (Si substrate) 3 which comprises the MUT element is covered with an oxide film ($SiO_2$) (insulation film 11). In each cell, the membranes 5 having the upper electrode 10 are supported by the piezoelectric supporting members 91 disposed at both ends of the cell. The membranes 5 are made of SiN.

The bottom electrode 7 is arranged so that it does not face the drive electrode 90 on the surface of the substrate 3 between the piezoelectric supporting members 91, and the insulation film 82 is formed thereon. The drive electrode 90 is formed on the insulation film 82.

On the upper surface of the drive electrode 90, the piezoelectric supporting members 91 are formed. The piezoelectric supporting member 91 contacts the upper electrode 10. The cavities 6 are the spaces enclosed by the upper electrode 10, the piezoelectric supporting member 91, and the insulation film 82 in FIG. 10.

The membrane 5 of each cell according to the present embodiment is separated from the membranes of the adjacent cells by the interstices 60, and is independent. Also, the MUT according to the present embodiment has the piezoelectric supporting members 91 along the nodes of the fundamental vibrations obtained when the membranes 5 vibrate freely as well as the second embodiment. The piezoelectric supporting member 91 is made of a single layered or stacked layered structure of, for example, aluminum nitride, zinc oxide, barium titanate, barium strontium titanate, or the like.

For the insulation film 82, materials having a high dielectric constant such as $SrTiO_3$, barium titanate ($BaTiO_3$), barium strontium titanate, tantalum pentoxide, niobium oxide stabilized tantalum pentoxide, oxidized aluminum, oxidized titanium ($TiO_2$), or the like are used.

Figure 11A:
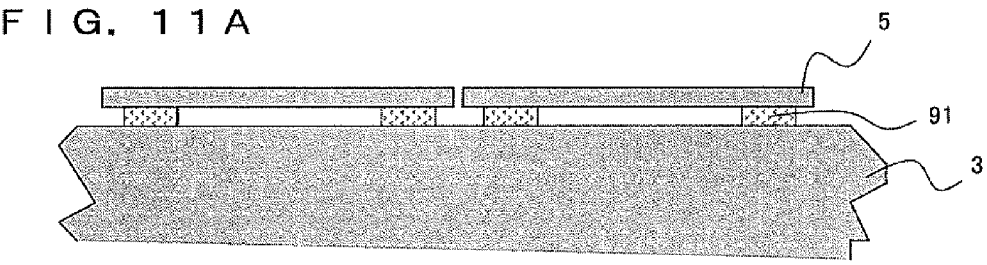
FIG. 11A is the first operation principle view of the MUT according to the fifth embodiment.
Figure 11B:
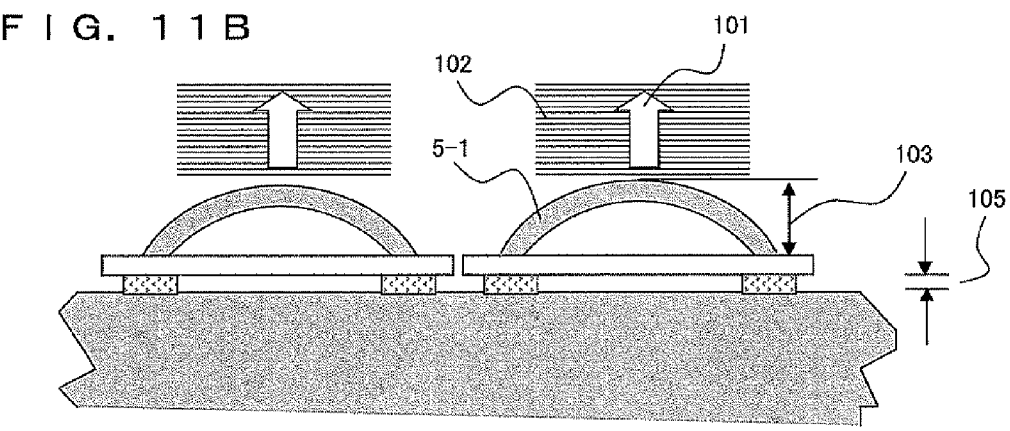
FIG. 11B is the second operation principle view of the MUT according to the fifth embodiment.
Figure 11C:
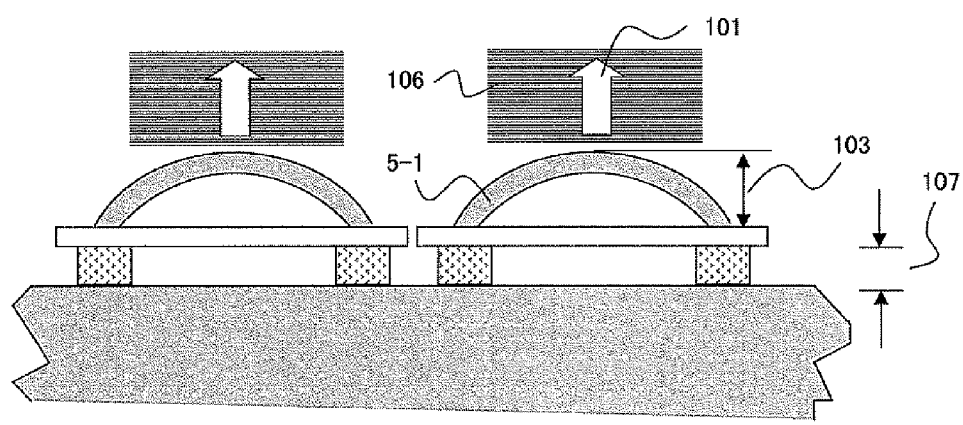
FIG. 11C is the third operation principle view of the MUT according to the fifth embodiment.

FIGS. 11A, 11B, and 11C show the operation principles of the MUT according to the present embodiment. FIGS. 11A through 11C schematically show the MUT shown in FIG. 10. FIGS. 11A through 11C show the operation of obtaining greater sound pressure of transmission ultrasound with the piezoelectric supporting members 91 expanding and shrinking together with the vibrations of the membranes 5 in order to accelerate the pressure waves by the membrane vibrations.

In FIG. 11A, the voltage applied to the bottom electrode 7 for the electrostatic driving (electrostatic driving application voltage) is zero and the voltage applied to the drive electrode 90 (piezoelectric driving application voltage) for the piezoelectric driving is zero. Accordingly, deformation of neither the membrane 5 nor the piezoelectric supporting member 91 has occurred.

In FIG. 11B, the piezoelectric driving application voltage is zero, and the electrostatic actuation is caused by applying voltage only to the bottom electrode 7. In this case, only the deformation of the membrane 5 has occurred. Numeral 5-1 denotes the maximum bending deformation state of membrane. The deformation amount is denoted by numeral 103. By this bending deformation of the membrane 5, the ultrasound is transmitted toward the direction represented by an arrow 101. Numeral 102 denotes the ultrasound compression wave. The piezoelectric supporting member 91 does not deform. Numeral 105 denotes the height of the piezoelectric supporting member 91 when it is not deformed.

FIG. 11C shows a state in which the maximum voltage has been applied to the bottom electrode 7 and the drive electrode 90. Then, the electrostatic driving and the piezoelectric driving become the maximum. In other words, the deformation of the membrane 5 becomes the maximum, and also the deformation of the piezoelectric supporting member 91 becomes the maximum. Numeral 107 denotes the height of the piezoelectric supporting member in the maximum deformation state. Also, the ultrasound compression wave denoted by numeral 106 is compressed more than the ultrasound compression wave 102 because the bending deformation (5-1) of the membrane and the expansion deformation (107) of the piezoelectric elements are superposed. In other words, further greater sound pressure of sound source can be caused.

Also, when receiving ultrasound, the entirety of the membrane is used for receiving the ultrasound so that the pressure is applied also to the piezoelectric supporting members 91 that are supporting the membrane. Thereby, voltage is obtained by the piezoelectric effect in the supporting members. Accordingly, the piezoelectric supporting member 91 can also be used for the detection of the reception ultrasound.

However, when transmitting ultrasound, vibrations are not applied to the piezoelectric supporting member 91, and accordingly a detection signal based on the deformation of the membrane is not generated. Accordingly, because a feedback signal is not obtained, the self oscillating circuit does not cause the self-oscillation, and thus the circuit shown in FIG. 3 cannot be applied. However, when the positions of the piezoelectric supporting members 91 are set at the ends of the membrane, it is possible to convert the waves into short pulse waves by utilizing the feedback signals by using the circuit shown in FIG. 3 or by applying a vibration waveform that cancels the tailing portion of the pulse signal upon receiving it in order to perform the dumping on the tailing portions.

According to the present embodiment, it is possible to increase the level of the output of the output ultrasound by using piezoelectric elements for the supporting members in order to cause the vertical deformation of the membrane itself based on the elevation of the piezoelectric elements in addition to the deformation by the vibration of the membrane.

Sixth Embodiment

In the present embodiment, a MUT that uses piezoelectric elements as the members for supporting the membranes of the MUT consisting of the cMUT and the pMUT will be explained. This MUT corresponds to the MUT obtained by combining the first and fifth embodiments. Also, in the explanation below, the same constituent elements as in the above embodiments are denoted by the same numerals, and for the detailed explanation thereof, refer to the above embodiments.

Figure 12:
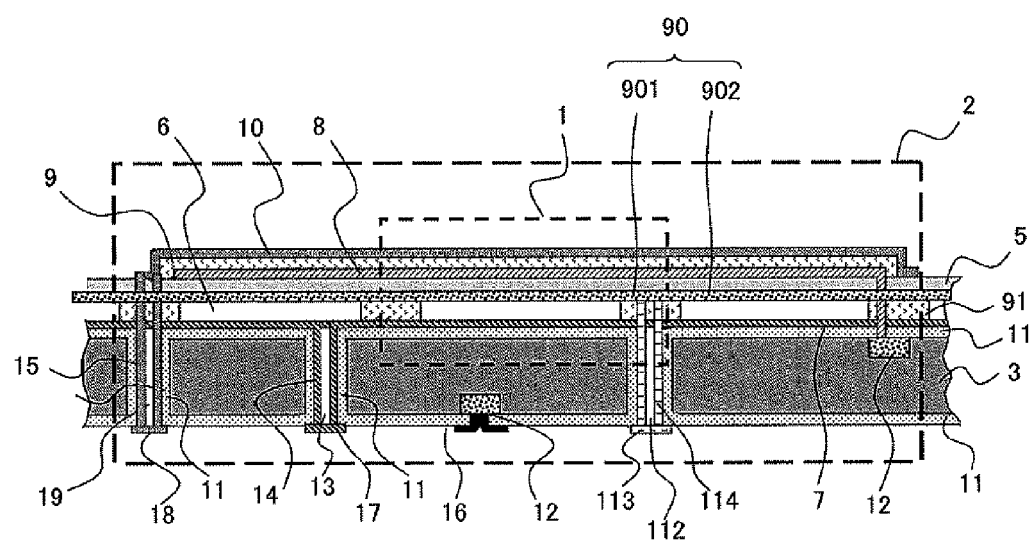
FIG. 12 is a cross-sectional view of a MUT according to the sixth embodiment.

FIG. 12 is a cross-sectional view of the MUT according to the present embodiment. The MUT shown in FIG. 12 is a micromachined ultrasound transducer. The MUT shown in FIG. 12 is a device in which piezoelectric elements (piezoelectric supporting members 91) are used as the supporting members 4 in the MUT in FIG. 1. In order to cause these piezoelectric supporting members 91 to function, a through hole 112 is made on the substrate 3, and a through hole wire 114 is formed on the side wall thereof. The piezoelectric supporting member 91 and a drive electrode pad 113 for driving the supporting member 91 are electrically continuous to each other via the through hole wire 114.

The drive electrode 90 includes an electrode 901 serving as an electrode of the upper surface side of the piezoelectric supporting member 91 and a wire 902 arranged so that it does not face the bottom electrode 7. In other words, in order to avoid the interference of the electric field caused by the bottom electrode 7, the wires 902 are not arranged above the cavity or the electrode 7.

On the upper surface side of the piezoelectric supporting member 91, the electrode 901 is formed, and on the bottom surface side thereof, a ground electrode (ground electrode for piezoelectric supporting member) that is not shown in the figure is formed. On the upper surface of the drive electrode 90, the membrane 5 is formed.

The drive electrode 90 is electrically continuous to the drive electrode pad 113 on the back surface side of the substrate 3 via the through hole wire 114 arranged in the through hole 112, and accordingly the driving voltage can be applied to the drive electrode 90 independently from the application of voltage to the bottom electrode 7. Also, the scope of the present invention is not limited to this, and it is possible to employ a configuration in which the drive electrode 90 is connected so that it has the same potential as the common ground electrode 8, and in which the bending vibrations of the membrane 5 and the thickness vibration of the piezoelectric supporting member 91 synchronize each other.

Also, in FIG. 12, the drive electrode 90 and the through hole wire 15 are arranged so that they do not is cross each other. Also, an insulation film (not shown) is formed on both or one of the surfaces of the cavity side of the bottom electrode 7 and the drive electrode 90 in order to avoid a short circuit between the electrodes. Also, although it is not shown for the sake of keeping the figure simple, insulation materials are arranged between the wires from the piezoelectric film 9, the common ground electrode 8, and the electrode 901 for the piezoelectric supporting member 91 so that these wires are not continuous to each other or with the respective electrodes.

Figure 13:
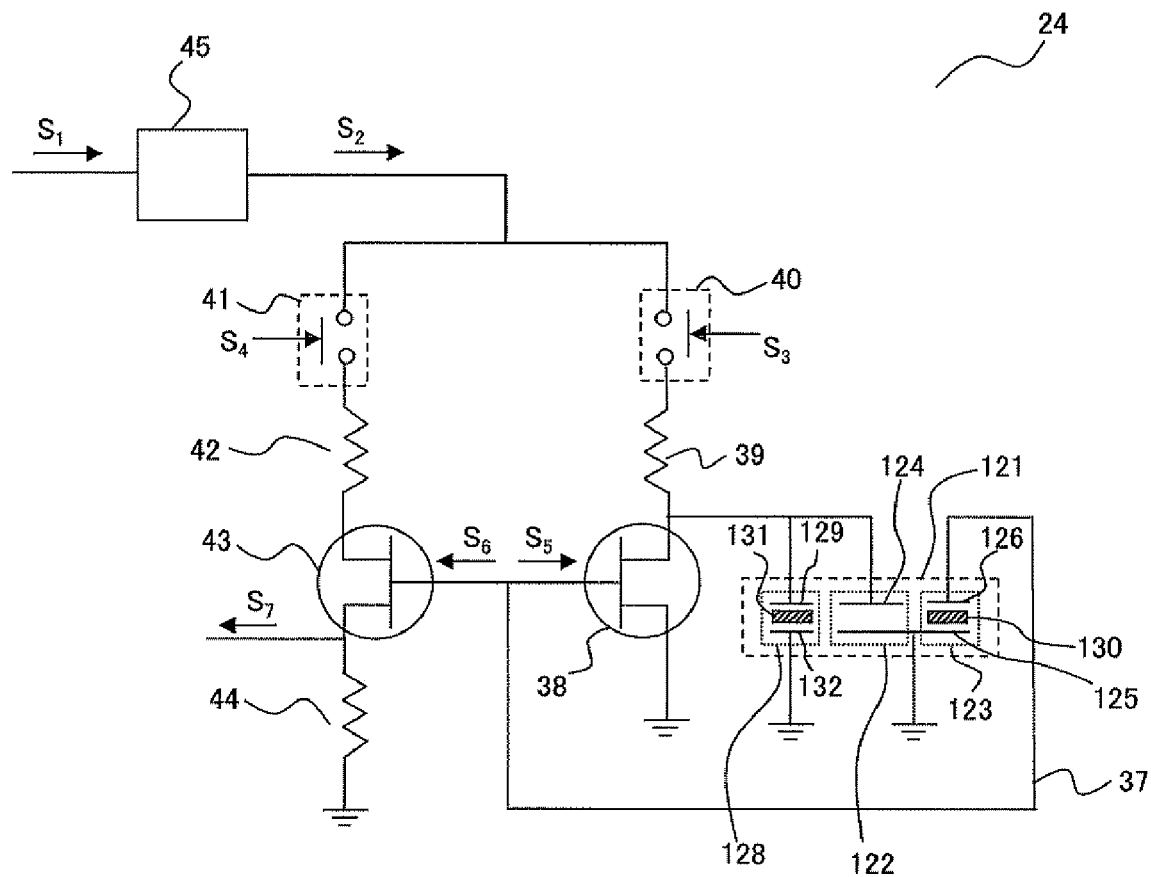
FIG. 13 shows a circuit configuration of the ultrasound probe 24 according to the sixth embodiment.

FIG. 13 shows a circuit configuration of the ultrasound probe 24 according to the present embodiment. The circuit shown in FIG. 13 is obtained by replacing the MUT 31 shown in FIG. 3 with the MUT shown in FIG. 12.

A MUT 121 schematically shows the MUT shown in FIG. 12. The MUT 121 includes a cMUT 122, a pMUT 123, and a thin film piezoelectric transducer 128. A common ground electrode 125 is a common ground electrode for the cMUT 122 and the pMUT 123.

The cMUT 122 includes a bottom electrode 124 and the common ground electrode 125. The cMUT 122 corresponds to a portion consisting of the bottom electrode 7, the cavity 6, and the common ground electrode 8 in FIG. 12.

The pMUT 123 includes an upper electrode 126, a piezoelectric film 130, and the common ground electrode 125. The pMUT 123 corresponds to a portion consisting of the upper electrode 10, the piezoelectric film 9, and the common ground electrode 8 in FIG. 12.

The thin film piezoelectric transducer 128 includes a drive electrode 129 for driving a piezoelectric supporting member, a piezoelectric film 131, and a ground electrode 132 for a piezoelectric supporting member. The thin film piezoelectric transducer 128 corresponds to a portion consisting of the drive electrode 90, the piezoelectric supporting member 91, and the ground electrode for piezoelectric supporting electrode (not shown) in FIG. 12.

Also, in FIG. 12, a self oscillating circuit includes the MUT 121, the FET 38, and the transmission line 37.

The operations of transmission and reception of the ultrasound beams of the Endoscopic ultrasound diagnosis system 1 according to the present embodiment will be explained.

When receiving the ultrasound beams, a switch control signal generator (not shown) performs control so that the switch SW40 is turned on on the basis of the SW control signal $S_3$ and the switch SW41 is turned off on the basis of the SW control signal $S_4$.

The AC signal (alternating voltage signal) $S_1$ is transmitted from the observation device 22 via the coaxial cable in the insertion tube 23, and is input into the AC-DC convertor 45. The AC-DC convertor 45 converts low-voltage AC signals into high-voltage AC signals, and outputs the DC high voltage signal 52 by using a high-voltage diode or the like.

The DC voltage $S_2$ is applied to the bottom electrode 124 of the cMUT 122 and the drive electrode 129 of the thin film piezoelectric transducer 128 through the SW 40 and resistor 39. Then, the membrane 5 is deformed by the electrostatic force generated between the bottom electrode 124 and the common ground electrode 125 (see FIG. 11B). Also, the piezoelectric film 131 is deformed by the piezoelectric effect of the piezoelectric film 131 caused by the voltage applied between the drive electrode 129 and the ground electrode 132 (see FIG. 11C). In other words, similarly to the fifth embodiment, the bending deformation of the membrane 5 and the expansion deformation of the piezoelectric film are superposed.

Accompanying the deformation of the membrane 5, the piezoelectric film 130 provided on the upper surface of the membrane 5 is also deformed. Then, the voltage signal $S_5$ is generated by the piezoelectric effect based on the deformation of the piezoelectric film 130. The voltage signal $S_5$ is input, via the feedback signal transmission line 37, into the gate (G) of the FET 38 as the feedback signal $S_5$.

When the feedback signal $S_5$ is input into the gate (G) of the FET 38, the drain (D) and the source (S) of the FET 38 become electrically continuous to each other, and accordingly the voltage that has been applied to the bottom electrode 124 of the cMUT 122 becomes zero. Then, the force that was applied to the membrane 5 of the cMUT 122 also becomes zero. Then, the load on the piezoelectric film 46 of the pMUT 123 side also becomes zero, and accordingly the voltage signal based on the piezoelectric effect of the pMUT 123 is not generated and thus the feedback signal $S_5$ is not output from the upper electrode 126. Then, the gate voltage of the FET 38 becomes zero, and the electrical continuity between the drain and the source is cancelled, and the DC voltage signal $S_2$ is again applied to the bottom electrode 124 of the cMUT 122. During the ultrasound transmission, this phenomenon is repeated.

By causing the positive feedback of the feedback signal, the self oscillating circuit can obtain the oscillation frequency of the self oscillating circuit during the ultrasound transmission. Accordingly, the vibration of the MUT is stabilized at the resonance frequency. As a result of that vibration of the membrane caused by the vibration operation, ultrasound is generated, and ultrasound is transmitted toward the upward direction of the upper electrode 36.

Next, when receiving ultrasound, the switch control signal generator (not shown) that has received the control signal from the observation device 22 performs control so that the switch SW40 is turned off on the basis of the SW control signal $S_3$ and the switch SW41 is turned on the basis of the SW control signal $S_4$.

When the MUT 121 has received ultrasound, the vibration of the ultrasound beam is propagated to the piezoelectric film 130 of the pMUT 123, and is converted into electric signals (pulse echo signal $S_6$) by the piezoelectric effect. The pulse echo signal $S_6$ is input into the gate (G) of the FET 43. Thereby, the pulse echo signal $S_6$ is amplified, is output from the source (S) side of the FET 43, and is output as a pulse echo signal $S_7$ to the observation device 22 via the coaxial cable.

In the above explanation, the voltage signal obtained by the piezoelectric effect of the piezoelectric film at the time of receiving ultrasound is a pulse echo signal; however, by obtaining the charges that can be obtained in the upper electrode (the common ground electrode 35 in FIG. 3) of the cMUT and detecting them together with a voltage that can be obtained by the piezoelectric film similarly as in the conventional techniques, it is possible to increase the reception sensitivity.

Figure 14:
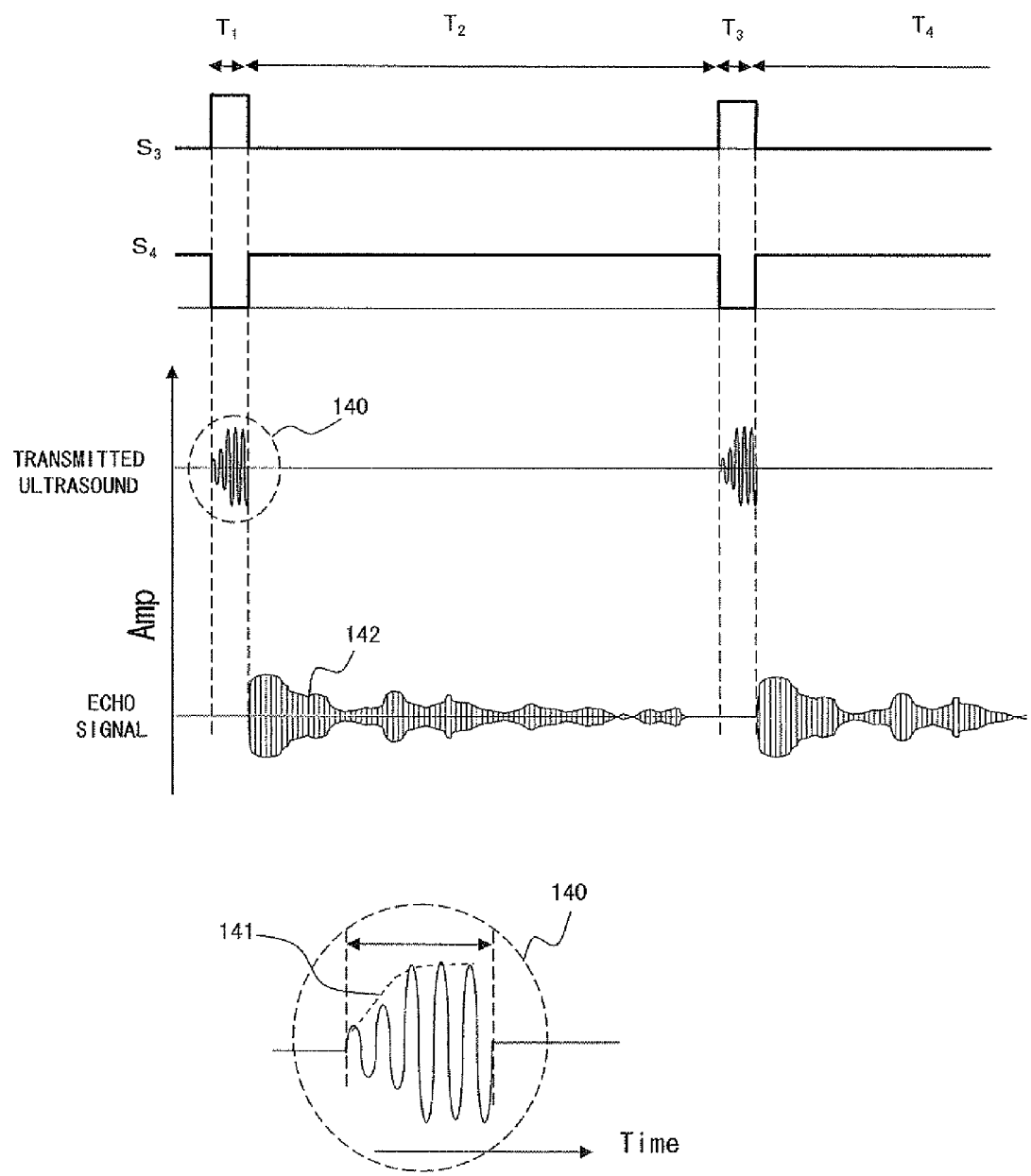
FIG. 14 is a timing chart of the switch (SW) operations and the ultrasound wave transmission driving voltage signal according to the sixth embodiment.

FIG. 14 is a timing chart of the switch (SW) operations and the ultrasound wave transmission driving voltage signal according to the present embodiment. By referring to FIG. 13, FIG. 14 will be explained. As shown in FIG. 14, the ultrasound wave transmission time periods ($T_1$, $T_3$, . . . ) and the echo signal reception time periods ($T_2$, $T_4$, . . . ) are repeated.

At the timing $T_1$, the SW40 is turned on by the SW control signal $S_3$ ($S_3$=ON), and the SW41 is turned off by the SW control signal $S_4$ ($S_4$=OFF). As explained in FIG. 13, ultrasound signals are output from the MUT 121. A waveform 140 represents a signal waveform of the ultrasound transmitted from the MUT 121. The lower figure of FIG. 14 is an enlarged view of the waveform 140. The waveform denoted by numeral 141 represents an envelope waveform formed on the basis of the peak values of the amplitude waveform of the transmitted waveform.

Next, at the timing 12, the SW40 is turned off by the SW control signal $S_3$ ($S_3$=OFF), and the SW41 is turned on by the SW control signal $S_4$ ($S_4$=ON). As explained in FIG. 13, the ultrasound is received by the MUT 121, and the ultrasound signal is converted into electric signals by the piezoelectric film. Numeral 142 denotes the waveform of the received echo signal.

Also, in FIG. 14, the scale of the amplitudes of the waveform 140 and the waveform 142 are expressed to the same extent for the purpose of explanation. However, the scale of the amplitude of the waveform 142 is actually considerably small compared to the waveform 140.

According to the present embodiment, the effect of the combination of the first and the fifth embodiments can be obtained. In other words, during the transmission of ultrasound, the self oscillating circuit causes the positive feedback of the feedback signals, and can obtain the resonance frequency of the self oscillating circuit. Accordingly, the vibration of the MUT becomes stabilized at the resonance frequency. Further, the output level of the output ultrasound can be increased by the vertical deformation of the membrane itself caused by the elevation of the piezoelectric elements in addition to the deformation caused by the vibrations of the membrane.

Also, in the present embodiment, the voltage applied to the bottom electrode of the cMUT is equal to the voltage applied to the driving electrode; however, they may be different from each other.

As described above, according to the present invention, when transmitting ultrasound, the output level of the ultrasound is increased by the synergistic effect between the electrostatic effect of the cMUT and the piezoelectric effect of the pMUT. Also, when receiving ultrasound, the reception sensitivity can be increased by the piezoelectric effect of the pMUT or by the piezoelectric effect of the pMUT and the electrostatic effect of the cMUT. Further, when receiving ultrasound, piezoelectric charges generated in the pMUT are utilized so that there is an effect such that a high DC bias voltage does not have to be applied continuously.

The MUT according to the present invention can be produced on a Si substrate by using the micromachining process, and accordingly it is possible to form the FETs 38 and 43, the resistors 39, 42, and 44, the SWs 40 and 41, and the AC-DC convertor 45 on or in the Si substrates on which the MUT is formed. Thereby, it can be made to be further compact.

Further, the ultrasound transducer according to the present invention can be included in Endoscopic ultrasound diagnosis systems such as an ultrasound endoscope, a miniature ultrasound probe, an intravascular ultrasound probe, or an ultrasound capsule endoscope. Also, in contrast to the conventional techniques, a high-voltage DC bias does not have to be applied, and accordingly it is advantageous in view of the safety of the Endoscopic ultrasound diagnosis system.

Also, the scope of the present invention is not limited to the above embodiments, and various configurations and shapes can be employed without departing from the spirit of the present invention.

What is claimed is:

1. An ultrasound transducer device manufactured by using a micromachining process having an ultrasound transducer comprising:
    a first electrode into which a control signal for transmitting ultrasound is input;
    a substrate on which the first electrode is formed;
    a second electrode that is a ground electrode facing the first electrode with a prescribed space between the first and second electrodes;
    a membrane on which the second electrode is formed and which vibrates and generates the ultrasound when voltage is applied between the first and second electrodes;
    a first piezoelectric film formed on the second electrode formed on a surface of the membrane; and
    a third electrode that is connected to the first piezoelectric film and faces the second electrode via the piezoelectric film, said ultrasound transducer device comprising:
    a conversion unit boosting an alternating current low voltage signal conveyed from a conveying cable, and converting it into a direct current voltage signal;
    a first switching unit switching an electrical connection between the conversion unit and the first electrode;
    a self oscillating unit performing self oscillation on the basis of the direct current voltage signal input into the first electrode in order to drive the ultrasound transducer to transmit ultrasound;
    a reception signal processing unit performing a prescribed signal process on a reception signal created on the basis of the ultrasound received by the ultrasound transducer; and
    a second switching unit switching an electrical connection between the conversion unit and the reception signal processing unit.

2. The ultrasound transducer according to claim 1, wherein: the piezoelectric film is a piezoelectric material that does not contain lead.

3. The ultrasound transducer according to claim 2, wherein: the piezoelectric material is one of aluminum nitride, zinc oxide, barium titanate, and barium strontium titanate.

4. The ultrasound transducer device according to claim 1, wherein: the first switching unit and the second switching unit are respectively turned on and turned off when transmitting ultrasound, and are respectively turned off and turned on when receiving ultrasound.

5. The ultrasound transducer device according to claim 4, wherein: the first switching unit and the second switching unit are a pair of electronic switches.

6. The ultrasound transducer device according to claim 5, wherein: the first switching unit and the second switching unit are integrated on a surface of the substrate or in the substrate.

7. The ultrasound transducer device according to claim 1, wherein: the ultrasound transducer further comprises:
a piezoelectric supporting member for supporting the membrane formed of a second piezoelectric film; and
a fourth electrode into which the direct current voltage signal for driving the piezoelectric supporting member is input.

8. The ultrasound transducer device according to claim 1, wherein: the self oscillating unit:
is a positive feedback circuit including at least an amplification element for amplifying the feedback signal and the ultrasound transducer; and
inputs, into the amplification element as a feedback signal, a voltage signal generated from the first piezoelectric film corresponding to deformation of the membrane activated by applying the direct current voltage signal between the first electrode and the second electrode.

9. The ultrasound transducer device according to claim 8, wherein: the self oscillating unit further comprises: a phase adjustment element for adjusting phases of the feedback signal in a stage earlier than the amplification element.

10. The ultrasound transducer device according to claim 8, wherein: the self oscillating unit further comprises: a high-frequency wave removal unit removing a high-frequency wave corresponding to a high-order vibration mode.

11. The ultrasound transducer device according to claim 1, wherein: the reception signal processing unit includes:
a charge amplification unit detecting the reception signal that is a charge signal;
an impedance conversion unit converting the reception signal having a high impedance into a reception signal having a low impedance; and
a voltage amplification unit amplifying the voltage of the reception signal.

12. The ultrasound transducer device according to claim 1, wherein: the ultrasound transducer, the self oscillating unit, the reception signal processing unit, the first switching unit, and the second switching unit are integrated on the substrate.

13. An Endoscopic ultrasound diagnosis system including the ultrasound transducer device according to claim 1.

14. The Endoscopic ultrasound diagnosis system according to claim 13, wherein: the Endoscopic ultrasound diagnosis system is an ultrasound endoscope.

15. The Endoscopic ultrasound diagnosis system according to claim 13, wherein: the ultrasound transducer device is used as a miniature ultrasound probe inserted into a forceps opening of an endoscope.

16. The Endoscopic ultrasound diagnosis system according to claim 13, wherein: the ultrasound transducer device is used as an intravascular ultrasound probe.

17. The Endoscopic ultrasound diagnosis system according to claim 13, wherein: the ultrasound transducer device is used as an ultrasound capsule endoscope.

18. A method of controlling an ultrasound transducer device manufactured by using a micromachining process, comprising:
an ultrasound transducer including:
a first electrode into which a control signal for transmitting ultrasound is input;
a substrate on which the first electrode is formed;
a second electrode that is a ground electrode facing the first electrode with a prescribed space between the first and second electrodes;
a membrane on which the second electrode is formed and which vibrates and generates ultrasound when voltage is applied between the first and second electrodes;
a first piezoelectric film formed on the second electrode formed on a surface of the membrane; and
a third electrode connected to the first piezoelectric film and facing the second electrode via the piezoelectric film; and
a conversion unit boosting an alternating current low-voltage signal conveyed from a conveying cable, and converting it into a direct current voltage signal;
a first switching unit switching an electrical connection between the conversion unit and the first electrode;
a self oscillating unit performing self-oscillation on the basis of the direct current voltage signal input into the first electrode in order to drive the ultrasound transducer to transmit ultrasound;
a reception signal processing unit performing a prescribed signal process on a reception signal created on the basis of the ultrasound received by the ultrasound transducer; and
a second switching unit switching an electrical connection between the conversion unit and the reception signal processing unit, wherein:
when transmitting ultrasound, the first switching unit is turned on and the second switching unit is turned off;
an alternating current voltage signal for controlling vibration of the membrane is boosted by the conversion unit in order to convert it into a direct current voltage signal;
the direct current voltage signal is supplied to the self oscillating unit via the first switching unit; and
ultrasound is transmitted from the ultrasound vibration on the basis of the self oscillating unit.

19. The method of controlling an ultrasound transducer device according to claim 18, further comprising:
turning off the first switching unit and turning on the second switching unit when receiving ultrasound;
receiving ultrasound by the ultrasound transducer and converting the received ultrasound into an electric signal;
conveying the reception signal converted into the electric signal to the reception signal processing unit; and
amplifying the voltage of the reception signal by the reception signal processing unit, and performing impedance conversion.

* * * * *